United States Patent [19]

Pirkle et al.

[11] Patent Number: 5,080,795
[45] Date of Patent: Jan. 14, 1992

[54] SUPPORTED CHIRAL LIQUID MEMBRANE FOR THE SEPARATION OF ENANTIOMERS

[75] Inventors: William H. Pirkle, Champaign; Elizabeth M. Doherty, Villa Park, both of Ill.

[73] Assignee: Research Corporation Technologies, Inc., Tucson, Ariz.

[21] Appl. No.: 528,007

[22] Filed: May 23, 1990

[51] Int. Cl.$^5$ .................................... B01D 61/38
[52] U.S. Cl. ........................ 210/643; 210/654; 210/195.2; 210/257.2; 210/321.72
[58] Field of Search ............... 435/183, 280, 177, 179, 435/180, 182, 135, 136, 148; 210/634, 643, 644, 649-652, 653, 654, 195.2, 257.2, 321.6, 321.64, 321.72

[56] References Cited

U.S. PATENT DOCUMENTS 4,800,162 1/1989 Matson .................................. 435/183

Primary Examiner—Frank Sever
Attorney, Agent, or Firm—Scully, Scott, Murphy & Presser

[57] ABSTRACT

The invention relates to a process for the high yield, cost efficient means of separating enantiomers. The process utilizes a supported liquid membrane and a chiral carrier which selectively complexes with one of the two enantiomeric optical configurations. The invention is also directed to an apparatus adaptable to the continuous and staged separation of enantiomers. In one embodiment, the apparatus utilizes a semi-permeable barrier and source and receiving locations each of which may be kept at temperatures which facilitate the complexation and dissociation processes.

39 Claims, 6 Drawing Sheets

SUPPORTED CHIRAL LIQUID MEMBRANE FOR THE SEPARATION OF ENANTIOMERS

This invention was made in part with Government support through grant NSF CHE 87-14950 awarded by the National Science Foundation. The Government has certain rights in the invention.

BACKGROUND OF THE INVENTION

1. Field of the Invention

The present invention relates to a process for separating enantiomers. In particular, the process of the present invention separates enantiomers having different optical configurations, such as R-S or D-L, by enantioselective transport through a supported liquid membrane using a chiral acceptor or carrier. The invention further relates to an apparatus which allows for inexpensive and reliable large scale, continuous enantiomeric enrichment and separation.

2. Description of the Prior Art

Stereoisomers are those molecules which differ from each other only in the way their atoms are oriented in space. Stereoisomers are generally classified as diastereomers or enantiomers; the latter embracing those which are mirrorimages of each other, the former being those which are not. The particular arrangement of atoms that characterize a particular stereoisomer is known as its optical configuration, specified by known sequencing rules as, for example, either R or S, or D or L.

Though differing only in orientation, the practical effects of stereoisomerism are important. For example, the biological and pharmaceutical activities of many compounds are strongly influenced by the particular configuration involved. Indeed, many compounds are only of wide-spread utility when provided in a given stereoisomeric form. When diastereomers are involved, separation is generally not a significant problem because diastereomers have different physical properties, such as melting points, boiling points, solubilities in a given solvent, densities, refractive indices, etc. Hence, diastereomers may normally be separated from each other by conventional methods, such as fractional distillation, fractional crystallization, or chromatography.

Enantiomers, on the other hand, present a special problem because their physical properties are identical. They cannot as a rule—especially when in the form of a racemic mixture—be separated by ordinary methods: not by fractional distillation, because their boiling points are identical; not by conventional fractional crystallization, because (unless the solvent is optically active) their solubilities are identical; not by conventional chromatography because (unless the adsorbent is optically active) they are held equally onto the adsorbent. The problem of separating enantiomers is further exacerbated by the fact that conventional synthetic techniques almost always produce a mixture of enantiomers. When the mixture comprises equal amounts of enantiomers having different optical configurations, it is called a racemate; and separation of the racemate into its respective enantiomers—this separation being generally known as a resolution—is, therefore, a process of considerable importance.

Various techniques for separating enantiomers are known. Most, however, are directed to small analytical quantities, meaning that, other drawbacks aside, when applied to preparative scale amounts (the milligram to kilogram range) a loss of resolution occurs. Hand separation—the oldest method of resolution—is not only impractical but can almost never be used since racemates seldom form mixtures of crystals recognizable as mirror-images.

Another method, known as an indirect separation, involves the conversion of a mixture of enantiomers—the racemate—into a mixture of diastereomers. The conversion is accomplished by reacting the enantiomers with an optically pure chiral derivatizing agent. The resultant diastereomers are separated from each other by talking advantage of their different physical properties. Once separated, by, for example, fractional crystallization, or more commonly, chromatography, the diastereomers are re-converted back into the corresponding enantiomers, which are now optically pure. Though achieving the requisite separation, the indirect method suffers in that it is time-consuming and can require large quantities of optically pure derivatizing agent which can be expensive and is oftentimes not recoverable. Moreover, the de-derivatization step may itself result in racemization thus defeating the purpose of the separation earlier achieved.

A more current method which avoids some of the drawbacks attendant the indirect method is known as the direct method of separation. The direct method, much like the indirect method, involves the formation of a diasteromeric species. However, unlike the indirect method, this species is transient, with the stability of one species differing from the other.

In one application of the direct method, the mixture of enantiomers is allowed to interact with a chiral stationary phase, which, for example, could reside in a chromatographic column. The enantiomer that interacts more strongly with the chiral stationary phase than the other will have a longer residence time relative to the chiral stationary phase and hence a separation will occur. When the mode of interaction with the chiral stationary phase can be characterized, the elution order may be predicted. Examples of chiral stationary phases include those based on (L)-N-(3,5-dinitrobenzoyl)leucine, which is useful in separating enantiomers of N-aryl derivatized amino acids and esters and those based on (L)-N-(1-naphthyl)leucine which has been used to effectively separate N-(3,5-dinitrobenzoyl) derivatized amino compounds.

Although this particular embodiment of the direct method is amenable to preparative scale chromatographic separation, the monetary cost is high and the capacity for such separations is low. Thus this particular mode is not attractive for large scale development.

An alternate adaptation of the direct separation method entails the utilization of the chiral aspects of the stationary phase—such as the (L)-N-(1-naphthyl)leucine structure—as a chiral carrier; the chiral carrier having the ability to form a complex more favorably with certain enantiomeric optical configurations than others. Normally, these chiral carriers, also known as chiral acceptors, are used in conjunction with a membrane. A membrane in this context is a semi-penetrable boundary between two phases commonly known as source and receiving phases, either of which can be gaseous or liquid. The nature of the membrane is that it controls the diffusion of molecules from one phase to the other. Importantly, a membrane in this context is defined functionally, not structurally. Thus a liquid can serve as a membrane, and indeed such membranes have been investigated for use in enantiomeric separations. In general, the rate at which molecules are removed from the source phase and appear in the receiving phase is known as the rate of transport. The rate of transport is a function of the rate of diffusion which, in turn, is a function of the size of the molecule. The rate of transport in this regard is further dependent on the solubility of the molecule in the liquid membrane, and the temperature. Further, if the liquid membrane is a bulk liquid, i.e., an unsupported liquid, then the rate of transport is also dependent upon the rate of stirring, if any. If the liquid membrane is supported, i.e., held within the pores of a microporous support, then the rate of transport is further dependent upon the surface area of the membrane. As a rule, supported liquid membranes exhibit higher rates of transport than unsupported, or bulk, liquid membranes.

Although a liquid membrane alone may transport enantiomers via an achiral direct-diffusion mechanism, no separation of enantiomers will ordinarily occur. Separation can be obtained, however, by the addition of a chiral carrier molecule to the liquid membrane which will enhance the rate of transport. The chiral carrier not only enhances transport but, more importantly, it permits selective transport. The chiral carrier in this situation forms a complex with an enantiomer located at the interface of the liquid membrane and source phase (in which the enantiomeric mixture is found), thus increasing the solubility of these molecules in the membrane. Enantioselective transport occurs because, as in the chiral stationary phase, the interactions leading to complexation favor one enantiomeric optical configuration over the other. Hence the transport through the liquid membrane—facilitated by the increase in the solubility of the complex—discriminates, as respects the enantiomers, in favor of the isomer which can form the more stable complex. It is noteworthy that in certain situations, enantiomers may be transported across the membrane by both the chiral carrier-assisted mechanism and by the achiral direct-diffusion mechanism. The degree to which transport is dependent on the one over the other will influence the selectivity of the separation.

Liquid membranes can be utilized in various arrangements depending on the particular application desired. The common requirement for any liquid membrane is that it maintain a division between the source phase (containing the racemate) and the receiving phase (having an enrichment of a particular enantiomer). Liquid membranes configured in bulk form typically involve a container which holds the liquid membrane and a hollow cylinder which is partially immersed into the liquid membrane. The hollow cylinder acts to separate the source phase, e.g., the area circumscribed by the inside of the cylinder, from the receiving phase, e.g., the area around the outside of the cylinder.

Bulk liquid membranes, however, do not attain the desired degree of resolution required for practical application. For example, the use of bulk chloroform liquid membrane in the "chiroselective" transport of sodium mandelate using the chiral carrier (−)-N-(1-naphthylmethyl)-α-phenylethylamine results in an optical resolution of less than 10% with only 7% mass transfer. Bulk chloroform liquid membrane has also been used for the enantioselective transport of amino ester salts using a chiral crown ether as a chiral carrier. Optical resolution here is somewhat better, being 85% for p-hydroxyphenylglycine methyl ester with 10% mass transfer after 182 hours. Bulk liquid membranes have also been used in the enantioselective transport of norephedrin enantiomers with dimenthyl tartrate esters as chiral carriers to obtain a 28% enantiomeric excess of (1-S)-norephedrin after approximately 20% of the original mass had been transferred.

Higher rates of transport are obtained with the use of supported, rather than bulk, liquid membranes. A supported liquid membrane differs from a bulk liquid membrane in that the former is held within the pores of a microporous support, such as filter paper or a polymeric film, e.g., polypropylene film. For example, an ether liquid membrane supported on a polypropylene film using a chiral crown ether as a chiral carrier has been investigated in the enantioselective transport of amino esters; the highest enantiomeric excess here was reported at 91.6% for phenylglycine perchlorate. Enantiomeric enrichment has also been studied using a water-based liquid membrane supported on filter paper. With β-cyclodextrin as a chiral carrier; enantiomeric excesses here were in the range of 16–75%.

While the use of supported liquid membranes in enantiomeric separation holds promise, these processes have not yet been developed beyond the laboratory scale using analytic quantities and operating in a batch-wise fashion. That is, a supported liquid membrane process for large preparative separations has yet to be developed. The problem is two fold: not only do the known processes not provide the necessary rates of transport and degree of separation in a reasonable time period, but the type of apparatus needed, i.e., one that is simple in design, relatively inexpensive to construct and adaptable to continuous operation, is not available, partly because of the loss of resolution normally associated with a timely processing of larger quantities.

The apparatus typically used in supported liquid membrane separation devices consists of two cells, usually glass or a related material, between which is interposed the supported liquid membrane. These configurations only allow for the batch processing of small amounts and are clearly unacceptable for practical commercial work. Thus, there is a pressing need for a process and apparatus utile in the preparative scale separation of enantiomers.

SUMMARY OF THE INVENTION

The present invention overcomes the above inadequacies in enantiomeric separation. The invention is directed to a process which is simple in design, relatively inexpensive, adaptable to continuous separation, all the while providing a high level of enantiomeric separation. The novel process of the present invention involves the use of a chiral carrier to form a stable complex with a particular enantiomeric optical configuration within a supported liquid membrane. The complexation is facilitated, if desired, by temperature control and, once accomplished, the transport of the complexed enantiomer having the requisite optical configuration through the liquid membrane is enhanced. The practice of the inventive process also provides for the rapid transport of the stable complex containing the particular enantiomeric optical configuration away from the initial enantiomeric mixture. Once the stable complex is sufficiently removed from the remaining enantiomers, it is dissociated back into the chiral carrier and the corresponding enantiomer. The dissociation, if desired, may be facilitated through temperature control. The thus dissociated enantiomer may then be recovered, in an enriched amount as the process continues, as can the enantiomers which do not form the stable complex. The enrichment of the latter enantiomers which do not readily form a stable-enough complex, is due to the depletion of those enantiomers which do. Thus, these latter enantiomers have also been enriched due to the selective removal of some or all of their optical counterparts.

The present invention also relates to an apparatus useful in separating enantiomers having different optical configurations. The apparatus may be used in a staged fashion so as to continually increase the separation of the enantiomeric mixture. Further, the apparatus of the present invention is reliable and simple to construct, utilizing as a support for the liquid membrane, materials such as polymeric tubing or hollow-fibers.

The liquid membrane and chiral carrier may be recirculated from a reservoir to the source kettle to the receiving kettle and back again to the reservoir. During this circulation and recirculation, a chiral carrier can complex with an enantiomeric molecule contained in the source phase, carry it to the receiving phase where the complex is dissociated and the enantiomer collected, and eventually return to the source phase for further complexation.

Figure 1:
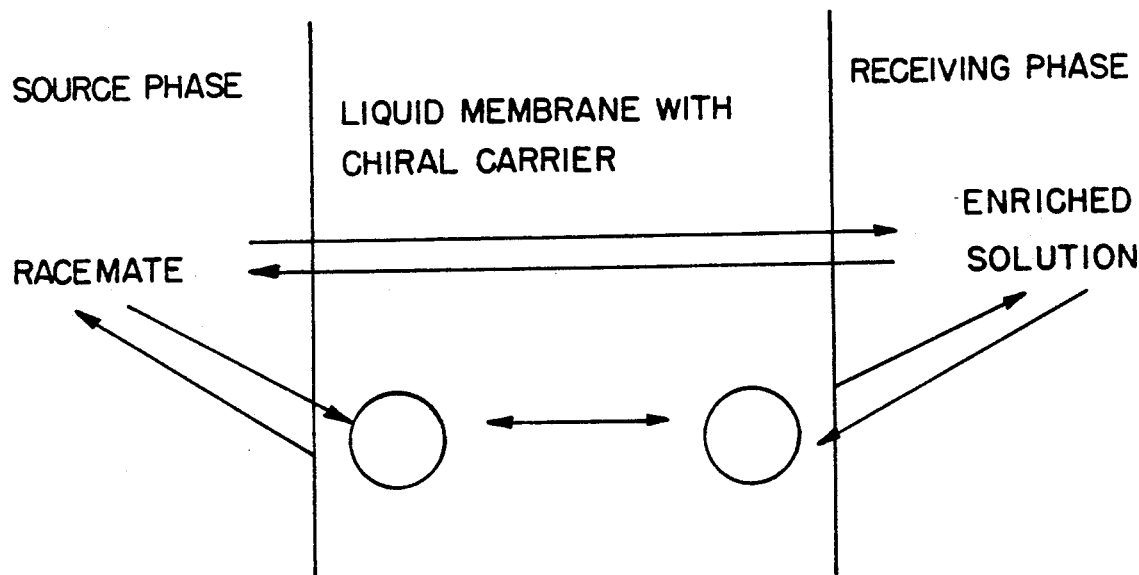
FIG. 1 depicts the transport process across a liquid membrane. The circles indicate a chiral carrier molecule which forms a more stable complex with one enantiomer than the other.
Figure 2:
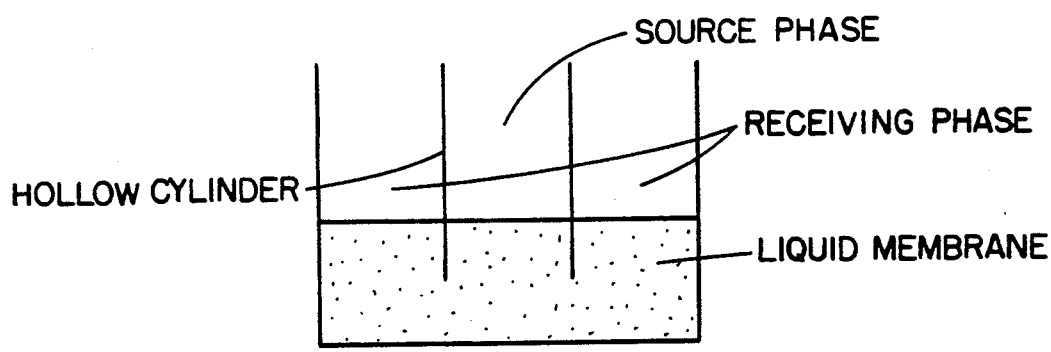
FIG. 2 depicts a typical configuration for enantiomeric separation using a bulk liquid membrane.
Figure 3:
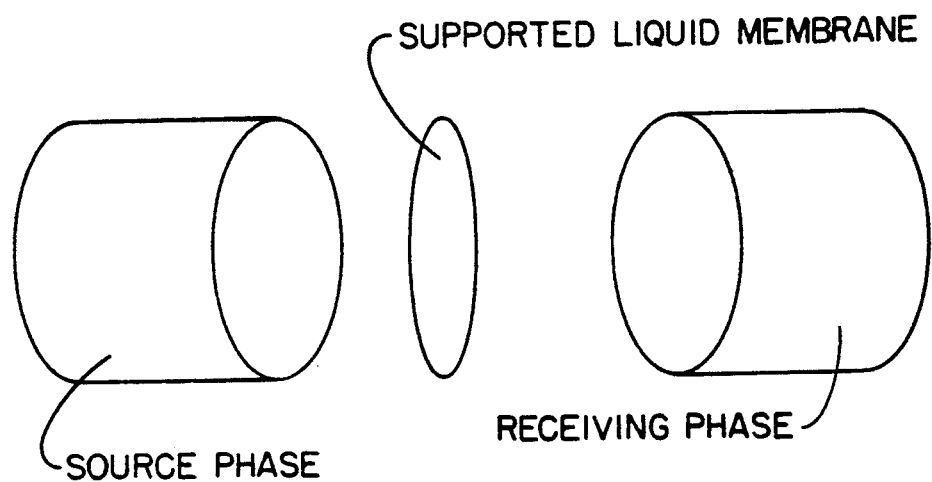
FIG. 3 depicts a typical apparatus for a supported liquid membrane in which the source and receiving phases are contained in glass chambers and the membrane is supported between them on a piece of filter paper. Access ports may be provided in the exterior wall of each cylinder.
Figure 4:
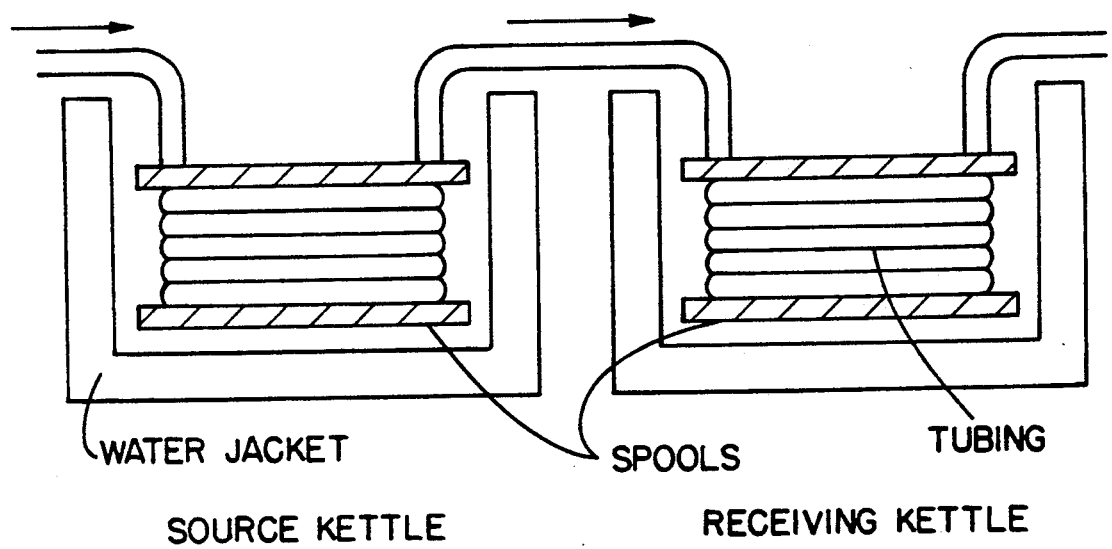
FIG. 4 depicts an embodiment of the apparatus of the present invention. It consists of a source and a receiving phase contained in separate, temperature-controlled vessels, sometimes known as kettles. A length of flexible, medical-grade, silicone rubber tubing is wrapped around two spools consecutively, and the spools are then immersed in the two kettles. The liquid membrane itself is pumped through the tubing. The chiral carrier solution is imbued in the pores of the walls of the tubing, generating an interface between the liquid membrane and the source and receiving phase, as depicted in FIG. 5. Thus, at the liquid membrane/source interface, the chiral carrier forms a complex with the analyte and the complex diffuses into the interior of the tubing where it is swept along by the flow of the liquid membrane. Diffusion occurs only within the pores of the tubing, the liquid membrane in the interior of the tubing serving only to store the analyte and carry it to the receiving kettle. In the receiving kettle, the complex diffuses to the receiving phase interface where the complex is then dissociated releasing the analyte into the receiving kettle and allowing the analyte to be collected.
Figure 5:
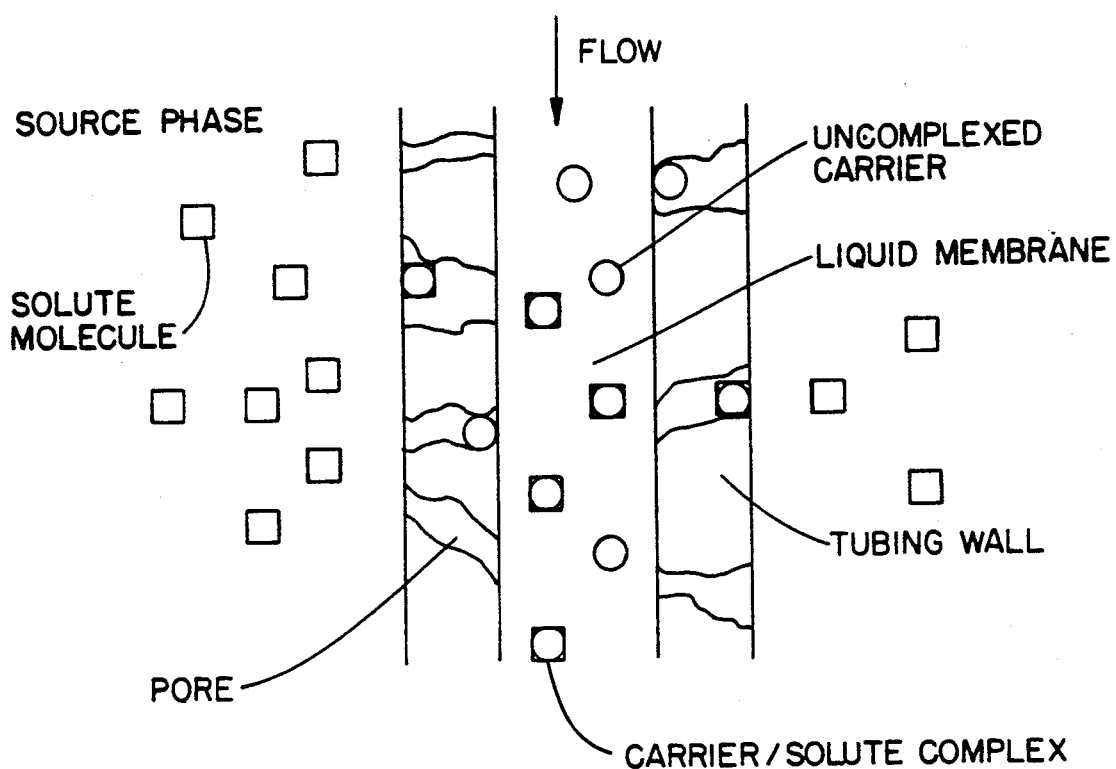

FIG. 5 illustrates an expanded cross-sectional view of the source phase/liquid membrane interface. The illustration does not indicate relative sizes of pores, solute and carrier. Diffusion occurs in the pores of the tubing only. The same process occurs in reverse in the receiving kettle.

Figure 6:
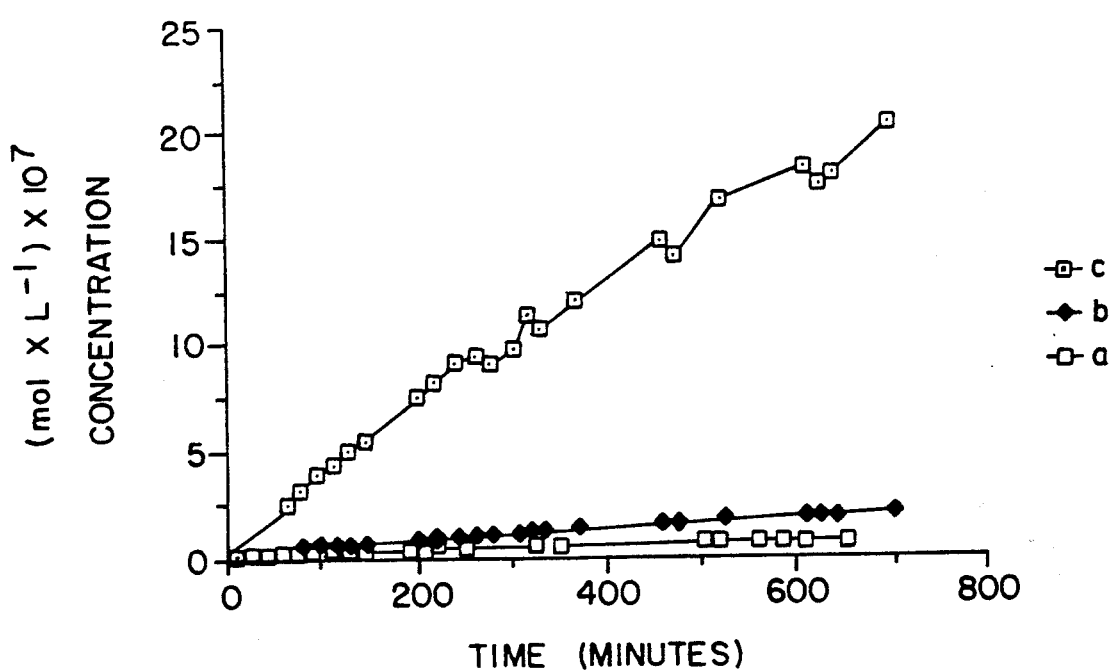

FIG. 6 is a graph of the change in concentration of N-(3,5-dinitrobenzoyl)leucine butyl ester in the liquid membrane over time. Curve a = R- and S- enantiomers, no carrier present; curve b = R-enantiomer, carrier present; curve c = S-enantiomer, carrier present.

Figure 7:
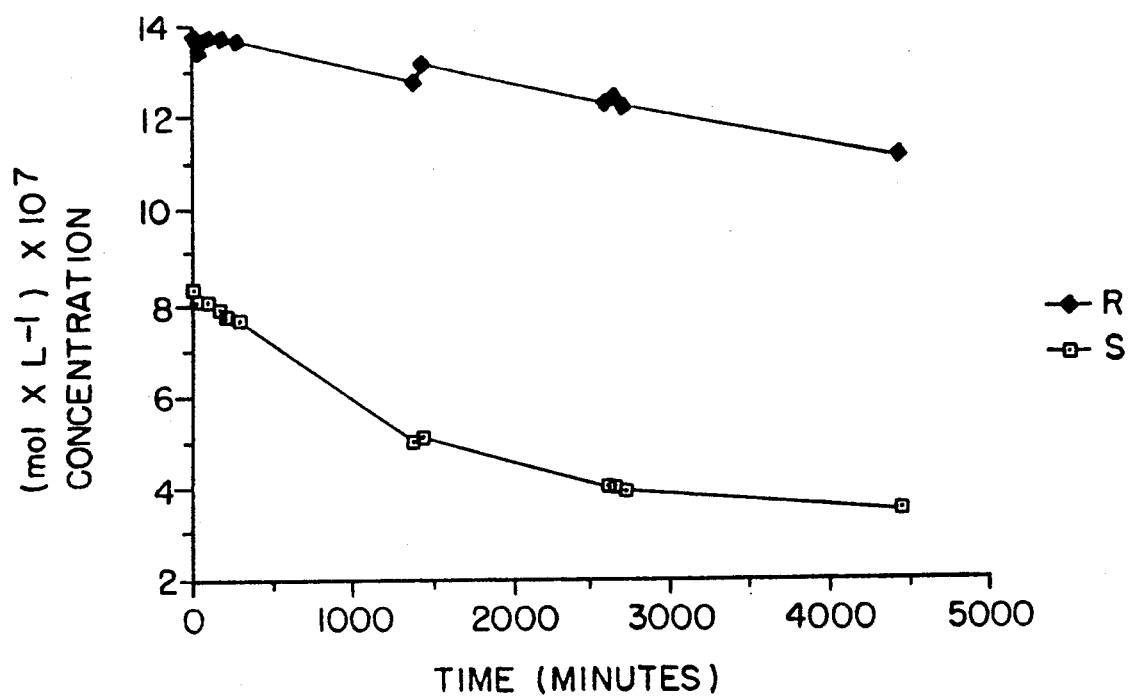

FIG. 7 is a graph of the decrease in the concentrations of the R- and S-enantiomers of N-(3,5-dinitrobenzoyl)leucine butyl ester over time in the first (source) kettle. An equilibrium between the source phase and the liquid membrane had been achieved by time zero. Concentrations are in units of $(mol \times 1^{-1}) \times 10^7$.

Figure 8:
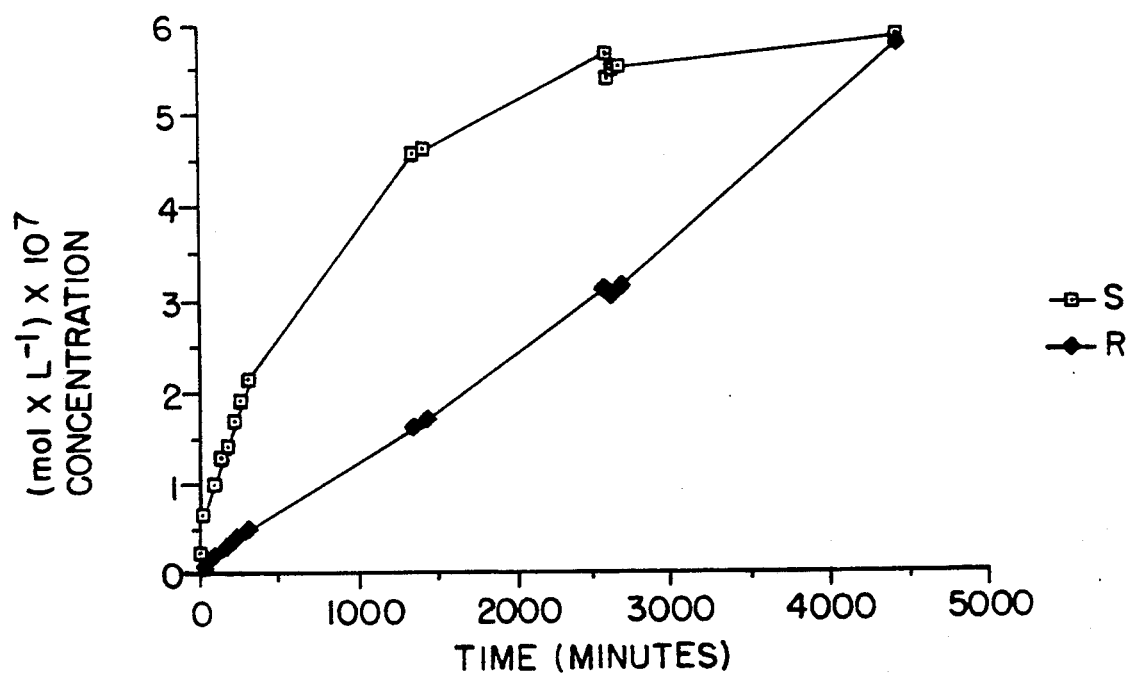

FIG. 8 is a graph of the increase in the concentrations of the R- and S-enantiomers of N-(3,5-dinitrobenzoyl)-leucine butyl ester over time in the second (receiving) kettle. An equilibrium between the source phase and the liquid membrane had been achieved by time zero.

Figure 9:
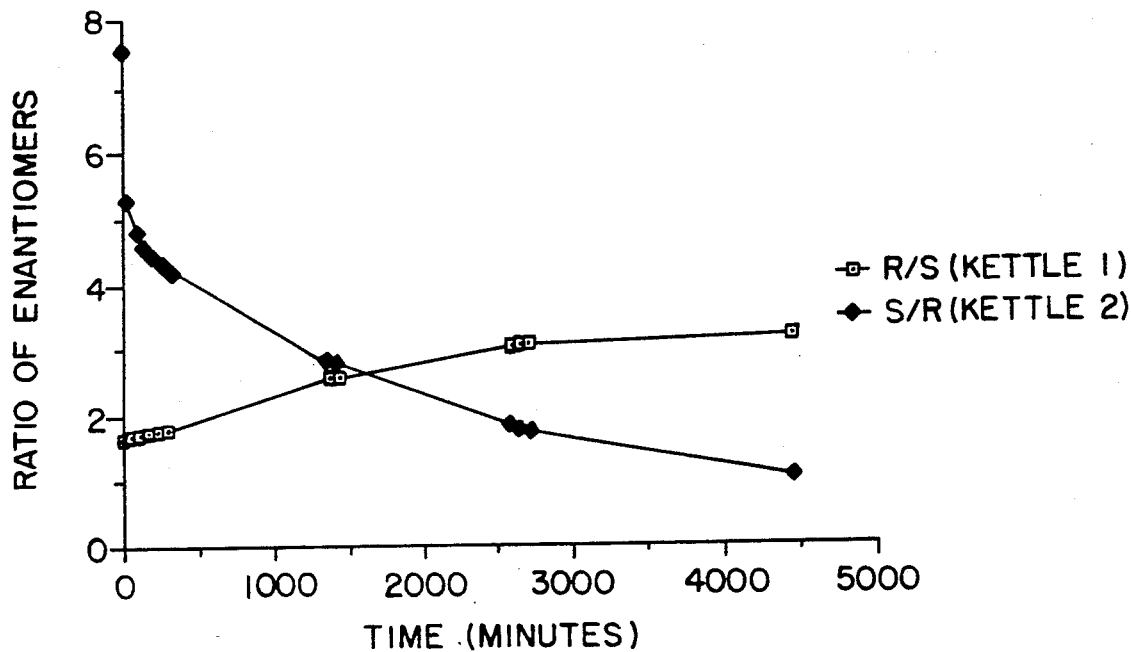

FIG. 9 is a graph of the change in the ratio of the enantiomers of N-(3,5-dinitrobenzoyl)leucine butyl ester in kettles 1 (source) and 2 (receiving) over time. An equilibrium had been achieved between the liquid membrane and the source phase at time zero.

Figure 10:
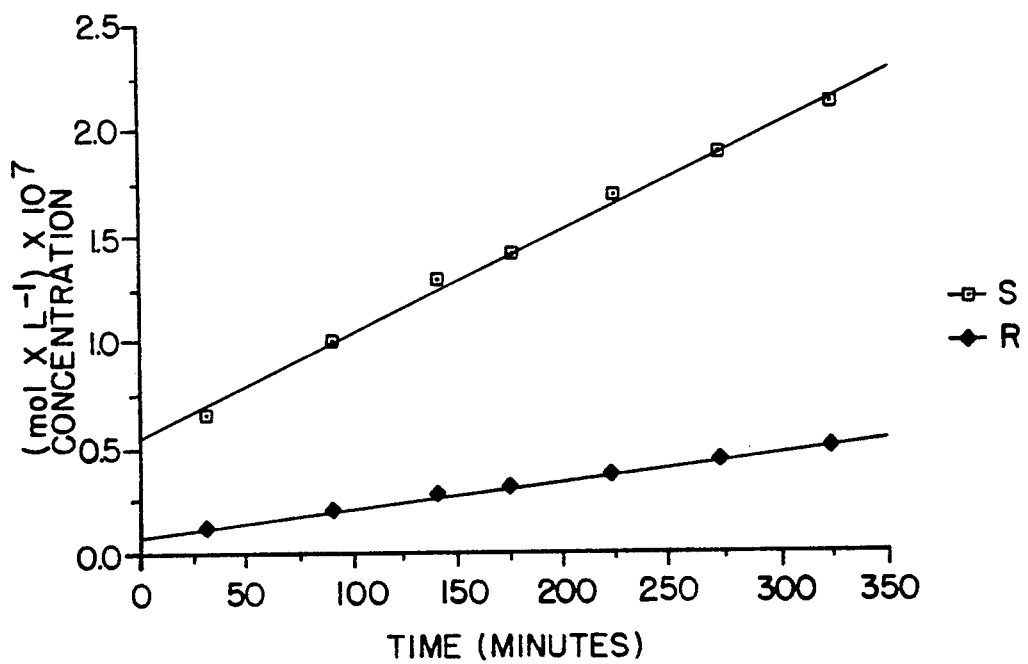

FIG. 10 is a graph of the change in the concentrations of (S) and (R) N-(3,5-dinitrobenzoyl)leucine butyl ester in the receiving phase during the first 350 minutes of transport.

Figure 11:
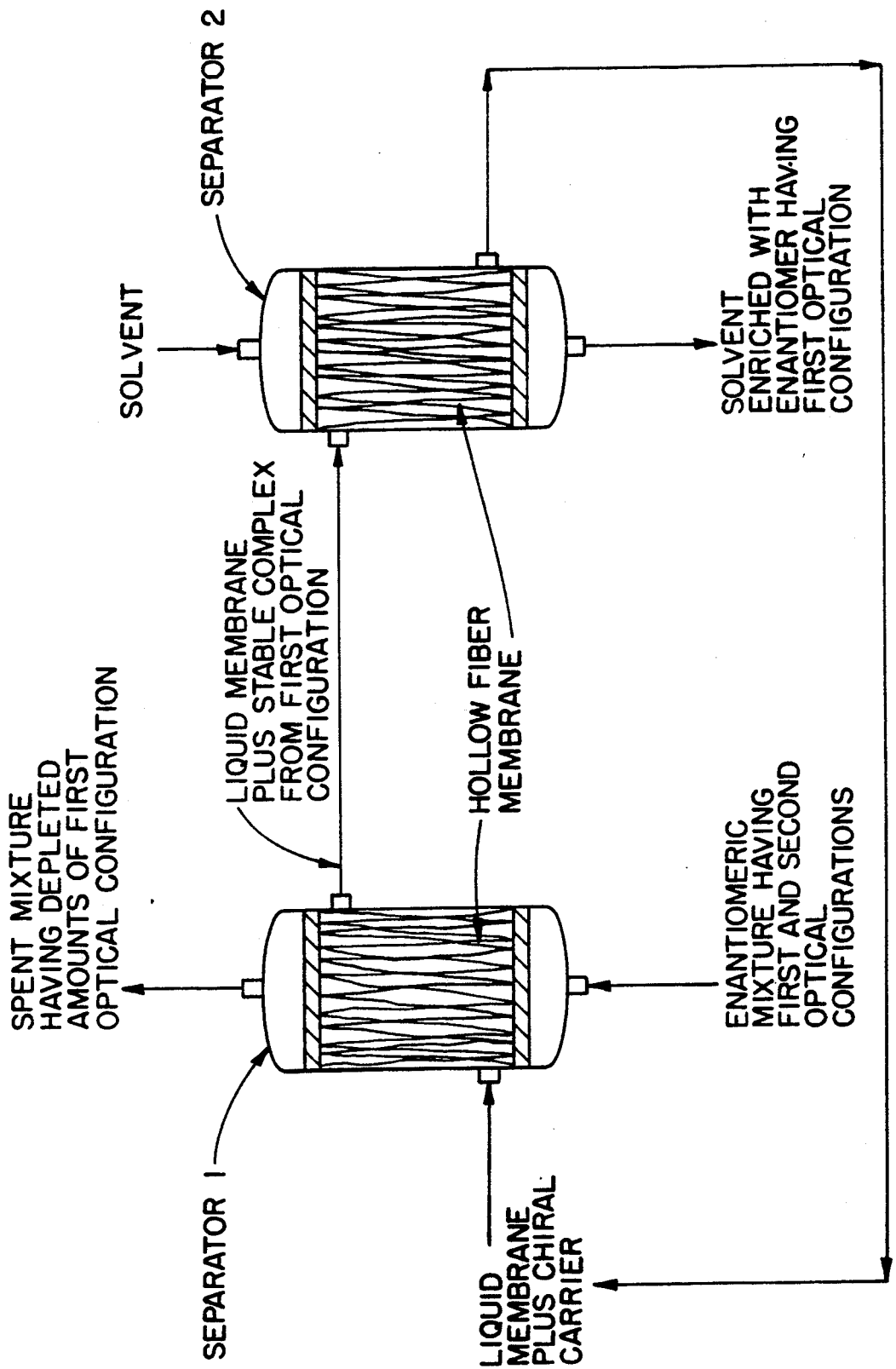

FIG. 11 depicts another embodiment of the present invention and illustrates enantiomeric separation utilizing hollow-fiber-membranes as a support or barrier. Separator 1 receives the liquid membrane-chiral carrier solution on the lumen side, and receives the enantiomeric mixture having first and second optical configurations on the shell side. The liquid membrane-chiral carrier solution impregnates the hollow fiber barrier in which is then formed a stable complex between the chiral carrier and an enantiomer having one optical configuration. The stable complex, once formed, passes into the liquid membrane solution and is transported to the lumen side of separator 2. On the shell side of separator 2 is introduced a solvent in which enantiomers having the one optical configuration are soluble. The stable complex and liquid membrane impregnate the hollow fiber barrier in separator 2 wherein the stable complex is dissociated. The enantiomer having the one optical configuration then passes from the hollow fiber barrier to the solvent and exits on the shell side for recovery or further processing downstream. The liquid membrane and chiral carrier which results from the dissociation may be recirculated back to separator 1 for reuse.

DETAILED DESCRIPTION OF THE INVENTION

The process of the present invention provides a practical method for the separation of mirror-image isomers utilizing enantioselective transport through a liquid membrane supported on a semi-permeable barrier. The transport mechanism is facilitated by the use of a chiral carrier, also known as a chiral acceptor or chiral transport agent, and can be further enhanced by proper temperature control of the complexation and dissociation steps involving the chiral carrier and the enantiomer having the optical configuration with which it preferably forms a complex. While the chiral carrier may well complex with both optical configurations present in the racemate, it forms a significantly more stable complex with only one configuration. Stable, in this sense, means that the particular complex is preferentially formed in amounts sufficient to provide a separation.

The barrier, or support, characterized as semi-permeable, must have the ability to provide a variety of functions. First, the barrier must be able to physically separate or substantially physically separate, the liquid membrane containing the chiral carrier from the workpiece solutions containing the enantiomers—either the racemate solution or the enriched downstream solution. The barrier must also be capable of being impregnated or substantially impregnated with the liquid membrane and chiral carrier, while not being so impregnated by the racemate or enriched enantiomeric solutions. Further, the barrier must be capable of allowing the stable complex to form within it, and permit the complex to pass from it to the liquid membrane (at least at that barrier or part of barrier in which forms the stable complex). The barrier must further be capable of allowing the stable complex to pass into it (at least at the barrier or part of barrier in which dissociation occurs) and to dissociate within it. This barrier must also permit the thus dissociated enantiomer to pass from it in order to be recovered.

Suitable semi-permeable barriers may be formed from either a microporous material or a gel-type material or a combination of both. The microporous barriers are those which have pores of a size which permit passage of the stable complex—which may be a moderately large compound—from one (or first) surface of the barrier to another (or second) surface of the barrier. The microporous barrier becomes impregnated via capillary action between the liquid membrane, which may contain the chiral carrier and/or the stable complex, and the pores, with complexation and dissociation occurring within the pores. In general, the larger the size of the pore, the greater the rate of transport; however, the pore size cannot be so large as to permit mixing between the enantiomeric solutions—the racemate and/or enriched solution—and the liquid membrane. Such mixing will adversely affect the selectivity of the system. Examples of microporous materials useful in the practice of the present invention include those formed from polysulfone and polyacrylonitrile; polypropylene, polyethylene or silicon rubber may also exhibit microporosity depending upon how these materials were processed. Combinations of these or like materials may also be used.

The gel-type barriers are those which are substantially non-porous, meaning they are free of discrete, well-defined pores. This type of material will generally become swollen when contacted with an appropriate fluid, such as the liquid membrane. When swollen, the gel-type barrier is impregnated with the liquid membrane, which may contain the chiral carrier and/or the stable complex. Complexation and dissociation occur within the swollen barrier. Examples of gel-type barriers, include those formed from regenerated cellulose; silicon rubber, polypropylene and polyethylene may also be considered as a gel-type barrier, depending upon how these materials were processed. Combinations of these or like materials may also be used. In general, microporous barriers are preferred to the gel-types for reason of higher permeability of the micropores to the larger species of stable complexes.

The support or barrier, regardless of its material of construction, must have at least two surfaces; one surface of which is in contact with the racemate solution at a first location (such as a source vessel) and with the solution to be enriched at a second location (such as a receiving vessel). At least another surface of the barrier must be in contact with the liquid membrane and preferably is configured to provide a flow path for the liquid membrane. The liquid membrane is normally a moving phase whose flow path is in the direction from the first, or source, location containing the racemates to the second, or enriched, location containing enantiomer separated by complexation with the chiral carrier. The preferred configuration of the barrier is that of a conduit. Most preferably, the barrier or support is configured as a tube or bundle of tubes or is in a hollow-fiber geometry.

The liquid membrane used for a particular separation will, of course, depend, in part, upon the racemate system—including the solvent in which the racemate is present—and may depend to some extent on circumstances relating to the barrier, such as porosity, and choice of chiral carrier. Generally, the liquid membrane may be polar or non-polar depending on these factors. When, for example, the racemate involves amino or like compounds, and/or when the barrier is silicone, the liquid membrane will preferably be a non-polar compound, such as an alkane. In these cases the liquid membrane is a $C_6$ to $C_{16}$ alkane, or mixtures thereof. Alkanes having lower freezing points, such as those exhibited by $C_{10}$ to $C_{14}$ alkanes are particularly attractive for larger scale systems: they reduce cost and permit the use of lower temperatures which can favorably effect complexation. To simplify the analytical evaluation of the performance of the system illustrated in the Examples, dodecane, a alkane to which silicone rubber is permeable, was used.

The choice of chiral carrier stems from the particular racemate involved and the particular optical configuration with which stable complexation is sought. Optical configuration, in this regard, refers broadly to the various designations known in the art to denote the configuration of the molecule. These include, for example, the D-L notations and the R-S notations. Generally, one having ordinary skill in the art can evaluate the capabilities of a particular chiral carrier/liquid membrane combination by way of partitioning experiments and in this manner develop a useful system without an undue amount of experimentation. In this way, the performance of the system in the process of present invention may be evaluated and steps to increase effectiveness may be developed.

For example, a chiral carrier may be chemically modified, e.g., by the addition of various functional groups, to increase its solubility in the liquid membrane, thus increasing the transport rate. To illustrate, the chiral carrier molecule (L)-N-(1-naphthyl) leucine octadecyl ester is useful in the separation of various derivatized amino compounds. This particular carrier was synthesized by the reaction scheme.

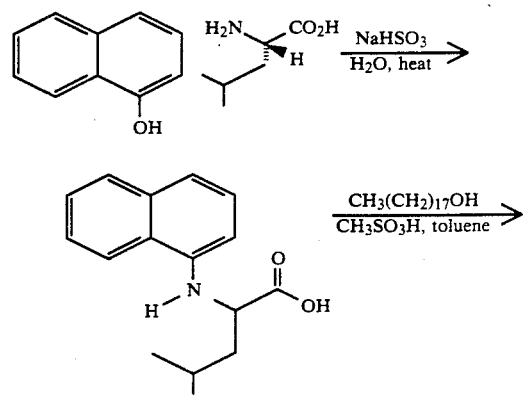

-continued

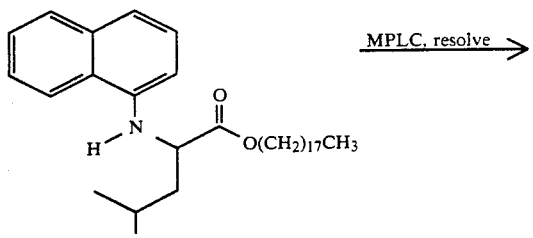

The N-naphthyl amino acid of this reaction was prepared by the Bucherer reaction of 1-naphthol with (L)-leucine. The octadecyl ester functionality was chosen because of its ability to increase the solubility of the resultant chiral carrier in a dodecane liquid membrane. Although some racemization occurred during the reaction sequence, optically pure carrier was obtained after removal of the optical impurity by medium pressure liquid chromatography (MPLC) on a stationary chiral phase based on (L)-N-(3,5-dinitrobenzoyl)leucine.

Once the candidate to serve as chiral carrier is selected, partition experiments may be undertaken to evaluate the ratio of the association constant, $K^S/K^R$, which is an indication of the inherent selectivity of the carrier for the racemic analytes, and to evaluate the ratio of enantiomers in the liquid membrane/chiral carrier solution, e.g., the S/R ratio, which is a reflection of the selectivity of the potential membrane. Once the various constituents are settled on relative to a particular enantiomeric separation, the process of the present invention may be employed to effect the desired separation.

The present process for separating enantiomers having first and second optical configurations involves providing a semi-permeable barrier, preferably configured in a tubular or in a hollow fiber geometry, that has at least a first and second surface; such as, for example, the inside surface and outside surface of a tube. In one embodiment, the semi-permeable barrier is provided such that it extends, in a contiguous fashion, from a first location to a second location; preferably the barrier is disposed, in part, within the first location and extends to the second location where it is again, in part, disposed. To increase the scale of separation, bundles of these barriers, such as tubes, may be used. In another embodiment, first and second permeable barriers are independently provided at the first and second locations, respectively. In this embodiment, the first and second barriers need not be contiguous, and may instead be connected by a conduit of a material which need not be semi-permeable.

The process of the present invention will now be described when, for illustrative purposes only, the racemate is a mixture of (±) N-(3,5-dinitrobenzoyl)amino esters or amides. The racemate, normally in solution form, is contacted with one surface of the barrier—in one embodiment, the outside of the tube—at the first location. The first location may be a container or source vessel for the racemate and solvent; preferably the solvent is a polar solution, such as water, or an alcohol-water or acetonitrile-water mixture. This is especially true when the liquid membrane is non-polar. Most preferably, a methanol-water mixture is used, particularly when dodecane is the liquid membrane. The ratio of the mixture may vary from about 10:1 methanol to water to all water; the optimal ratio varying from racemate to racemate. In the embodiment exemplified, the ratio is about 4:1 methanol to water. Contact between the racemate solution and the first surface of the barrier may occur, for example, by immersing part of the barrier, such as the outside of a tube, into the racemate solution.

At another surface of the barrier, not in direct contact with the racemate, a fluid, such as the liquid membrane, is passed. In this embodiment, the liquid membrane flows within a tube, the inside wall of which is the first barrier surface and the outside wall of which is the second barrier surface. The direction of the flow of the liquid membrane is from the first location or source vessel, to a second location. The second location may be a container, such as a receiving vessel, and is the location in which the enantiomer having the optical configuration amenable to stable complexation with the chiral carrier is released after dissociation with said chiral carrier. In a staged process, this second location may serve as a "first" location, or source vessel, for further downstream processing, using the process of the present invention, of the enantiomeric solution now enriched with the stable-complex-forming optical configuration. The "second" location of the downstream processing in turn may serve as the "first" location of still another downstream process. This repetitive processing of the continuously enriched solution may continue thus and so on to obtain a very high degree of enantiomeric separation. Depending upon whether the first and second locations are at different temperatures relative to each other, heat exchange may be required before commencing the downstream processing. For example, if, due to the association and dissociation constants, the first location is at 0° C. and the second location is at 50° C., the material within the second location must at some point be cooled so to most effectively utilize it as the "first" location for the downstream processing.

The second location, acting as a receiving vessel, preferably contains the same solvent used in the first location, such as, e.g., a 4:1 methanol-water mixture. It is into this solvent that the enantiomer having the stable-complex-forming optical configuration will be released after dissociation from the chiral carrier. The enantiomers at the receiving vessel may be recovered by, for example, causing the methanol-water mixture to evaporate.

The chiral carrier chosen for the particular racemate is interspersed within the pores of the barrier support. Preferably, the barrier—such as, e.g., the silicone tubing—has been soaked in the liquid membrane so to fill the pores of the barrier with the liquid membrane. One technique for imbuing a chiral carrier into a pore of the barrier is to place the carrier into the liquid membrane, the liquid membrane then being passed or pumped along the first, or inside, surface. The chiral carrier can thus enter a pore of the barrier from the flowing stream of liquid membrane.

At a first pore located within that part of the barrier at the first location, where the racemate contacts the outer surface of the barrier, complexation takes place; the complexation occurring at least between an enantiomer having a first optical configuration the first optical configuration being that which results in the stable form of the complex—stable as hereinbefore defined—and the chiral carrier. The chiral carriers may complex with both optical configurations of the enantiomer, but for adequate separation to occur, it must complex with the stable-forming configuration to a greater extent than with the enantiomers of the less-stable complex configuration. In this way, the chiral carrier in the context of the present invention is said to be enantioselective.

The formation of the stable complex occurs within this first pore of the barrier, the pore in which is situated the chiral carrier. This means that complexation may occur at any point from the interface of the racemate solution and the first pore (which interface is located at the outside surface) all the way to the interface of the liquid membrane and the first pore (which interface is located at the inside surface). The rate and extent of complex formation, otherwise known as the rate and extent of association between the chiral carrier and the enantiomer, is temperature dependent. By controlling the temperature, i.e., by maintaining temperature the source vessel at a higher or lower temperature—depending on the association chemistry of the particular system—the rate of the achiral transport process is slowed, while the rate and enantioselectivity of the carrier process is increased, owing to an increase in the association constant. Normally the temperature is lowered. Once the stable complex is formed, it is moved, by a combination of diffusion, solubility in the liquid membrane, and flow effects into the flowing liquid membrane. Once admixed with the liquid membrane the stable complex is transported to the second location or receiving vessel.

At the receiving vessel, the complex is dissociated. The dissociation occurs, preferably, within a second pore of the barrier located within that part of the barrier at the receiving vessel, or at the interface between this pore and the solution within the receiving vessel. Like the formation of the complex, the dissociation may be enhanced by proper temperature control. For example, by maintaining a higher or lower temperature at the receiver vessel—which temperature depends upon the dissociation chemistry of the particular system—one can increase the dissociation rate of the complex back into the chiral carrier and corresponding enantiomer as well as increase the rate of diffusion of the enantiomer out of the membrane and into the receiver. The particular chemistry of the system will determine how the temperature is controlled. Normally, the temperature of the second location is increased to achieve these effects.

Once dissociated and released out of the barrier, the enantiomers can be recovered from the receiving vessel by conventional means, such as evaporation. The result is an enantiomeric enrichment at the receiving vessel of that optical configuration that can form the stable complex, and an enrichment at the source vessel of the optical configuration that does not form the stable complex.

In another embodiment of the present invention, the enantiomeric separation is carried out in an apparatus utilizing hollow-fiber-membranes as the barrier or support. In this embodiment, hollow-fiber-membrane modules are used to obtain intimate, high surface area contact between the liquid membrane-chiral carrier and the racemate and enriched solution. This particular embodiment offers simple, passive, reliable, and easily scaled-up results and further provides operational flexibility in terms of, e.g., flow rate ratios and continuous operation. The hollow-fiber-membrane devices useful in the practice of this embodiment of the present invention are those described, for example, in U.S. Pat. No. 4,754,089, which is incorporated by reference herein.

The following examples will illustrate and describe without limiting the invention.

EXAMPLE 1

Synthesis of a Chiral Carrier

The chiral carrier (L)-N-(1-naphthyl) leucine octadecyl ester was synthesized as follows:

10g (L)-leucine (85 mmol), 12.3 g 1-naphthol (85 mmol), 10.8 g Na 6.25 g $NaHSO_3$, 6.25 g NaOH and 60 mL $H_2O$ were placed in a pressure vessel equipped with a magnetic stirrer. The reaction mixture was heated to 115° C. for three days, then allowed to cool to room temperature. The mixture was poured into a 1 L beaker and the vessel was rinsed with acetone and 2N $Na_2CO_3$ (20 mL each). The washings were added to the beaker and the mixture diluted to 500 mL with water. The pH was adjusted to 8.8-9.0 with saturated $Na_2CO_3$ (aq.). The mixture was washed twice with dichloromethane (50 mL each) to remove 1-naphthol. The dichloromethane washings were combined and extracted with 20 mL 5% $NaHCO_3$ which was then added to the aqueous phase. The dichloromethane was discarded. Concentrated HCl was used to adjust the pH of the aqueous phase to 3.0-3.5. The aqueous phase was extracted twice with ethyl acetate (100 mL each) and the combined extract was dried over $MgSO_4$ and concentrated. Crude yield: 5.77 g (26%).

One g crude N-(1-naphthyl)leucine and 1.05 g 1-octadecanol (3.9 mmol) were dissolved in 50 mL dry toluene and to this was added 3-5 drops methanesulfonic acid. The reaction mixture was heated to reflux and stirred overnight. Water was removed by azeotropic distillation using a Dean-Stark trap. The reaction mixture was cooled, diluted with dichloromethane and extracted with diluted $NaHCO_3$ (aq.) followed by water. The dichloromethane layer was dried over $MgSO_4$ and concentrated. Purification by flash silica gel chromatography (mobile phase: 4:1 hexane:dichloromethane) resulted in a yield of 1.77 g (89%) enantiomerically impure (L)-N-(1-naphthyl)octadecyl ester (oil). The optically pure carrier was obtained after MPLC purification using an (L)-N-(3,5-dinitrobenzoyl)leucine chiral stationary phase with mobile phase 5% 2-propanol in hexane (70% yield). The product was isolated as a yellow oil which had the following properties: $^1$H NMR (200 MHz, $CDCl_3$) $\delta 0.8$ (t,3H); $\delta 1.0$ (dd,6H); $\delta 1.2$ (s,30H); $\delta 1.6$ (m,2H); $\delta 1.8$ (m,2H); $\delta 1.9$ (m,1H); $\delta 4.1$ (t,2H); $\delta 4.3$ (t,1H); $\delta 4.7$ (broad s,1H); $\delta 6.6$-7.8 (m,7H). Anal Calcd for $C_{34}H_{55}NO_2$: C, 80.10; H, 10.88; N, 2.75. Found C, 80.45; H, 10.94; N, 2.60.

EXAMPLE 2

Synthesis of Amino Esters

Six different N-(3,5-dinitrobenzoyl)amino esters —namely, N-(3,5-dinitrobenzoyl)alanine n-butyl ester, N-(3,5-dinitrobenzoyl)valine n-butyl ester, N-(3,5-dinitrobenzoyl)-α-methyl-valine n-butyl ester, N-(3,5-dinitrobenzoyl)leucine methyl ester, N-(3,5-dinitrobenzoyl)leucine n-butyl ester, and N-(3,5,dinitrobenzoyl)-leucine n-octyl ester, were separately synthesized using the following reaction scheme.:

10 mmol of the corresponding amino acid was dissolved in dry tetrahydrofuran (THF) and cooled to 0° C. With stirring, propylene oxide was added followed by 10 mmol 3,5-dinitrobenzoyl chloride in portions. After addition was complete, the reaction mixture was allowed to warm to room temperature and stirred for two hours. The solvent was removed by evaporation under a vacuum. The crude N-(3,5-dinitrobenzoyl- )amino acid was dissolved in an excess of alcohol (such as methanol, n-butanol or n-octanol which alcohols can, for the most part, be used interchangeably. The higher alcohols, however, lead to esters showing less enantioselectivity but higher transport rates in the separation system exemplified), and to this was added 3-5 drops methanesulfonic acid. The mixture was refluxed overnight and water was removed via Dean-Stark distillation. The reaction mixture was then cooled, diluted with dichloromethane and washed twice with dilute NaOH and once with water. The organic phase was dried over $MgSO_4$ and concentrated. Purification was achieved by flash silica gel chromatography eluting first with 50% hexane:dichloromethane followed by dichloromethane. Yields were in the range of 10–78%.

(±)-N-(3,5-dinitrobenzoyl)alanine n-butyl ester was isolated as white needles from methanol/water and found to exhibit the following properties: mp 93–96° C.; 1H NMR (200 MHz, $CDCl_3$) δ1.0 (t,3H); δ1.4 (m,2H); δ1.6 (d,3H); δ1.7 (m,2H); δ4.2 (t,2H); δ4.8 (quint,1H); δ7.2 (d,1H); δ9.0 (d,2H); δ9.2 (t,1H).

(±)-N-(3,5-dinitrobenzoyl)valine n-butyl ester was isolated as white crystals from methanol/water and found to exhibit the following properties: mp 88°–91° C.; 1H NMR (200 MHz, $CDCl_3$) δ1.0 (m,9H); δ1.4 (sext,2H); δ1.7 (quint,2H); δ2.4 (m,1H); δ4.2 (t,2H); δ4.8 (q,1H); δ7.0 (broad d,1H); δ9.0 (d,2H); δ9.2 (t,1H).

(±)-N-(3,5-dinitrobenzoyl)-α-methyl-valine n-butyl ester was isolated as white crystals from methanol/water and found to exhibit the following properties: mp 110°–113° C.; 1H NMR (200 MHz, $CDCl_3$) δ1.0 (m,9H); δ1.4 (sext,2H); δ1.7 (m,2H); δ1.8 (s,3H); δ2.5 (sept,1H); δ4.2 (t,2H); δ7.2 (s,1H); δ9.0 (d,2H); δ9.2 (t,1H).

(±)-N-(3,5-dinitrobenzoyl)leucine methyl ester was isolated as white needles from methanol/water and found to exhibit the following properties: mp 143°–145° C.; 1H NMR (200 MHz, $CDCl_3$) δ1.6 (m,6H); δ1.8 (m,2H); δ3.8 (s,3H); δ4.9 (m,1H); δ6.8 (broad d,1H); δ9.0 (d,2H); δ9.2 (t,1H).

(±)-N-(3,5-dinitrobenzoyl)leucine n-butyl ester was isolated as white needles from methanol/water and found to exhibit the following properties: mp 95°–98° C.; 1H NMR (200 MHz, $CDCl_3$) δ1.0 (m,9H); δ1.4 (sext,2H); δ1.8 (m,5H); δ4.2 (t,2H); δ4.9 (m,1H); δ7.0 (broad d,1H); δ9.0 (d,2H); δ9.2 (t,1H).

(±)-N-(3,5-dinitrobenzoyl)leucine n-octyl ester was isolated as white crystals from methanol/water and found to exhibit the following properties: mp 71°–73° C.; MHz, $CDCl_3$) δ0.9 (t,3H); δ1.0 (d,6H); δ1.3 (m,10H); δ1.7 (m,5H); δ4.2 (t,2H); δ4.9 (m,1H); δ6.9 (broad d,1H); δ9.0 (d,2H); δ9.2 (t,1H).

EXAMPLE 3

Synthesis of Amino Amide

N-(3,5-dinitrobenzoyl)leucine n-butyl amide was synthesized as follows:

10 mmol racemic N-(3,5-dinitrobenzoyl)leucine was dissolved in dichloromethane and an excess of n-butyl amine. To this was added a catalytic amount of EEDQ and the mixture was sonicated in a water bath for 10 minutes. A pale yellow precipitate which exhibited the following properties was collected and dried. mp 215°–217° C.; 1H NMR (200 MHz, DMSO) δ 1.0 (m,9H); δ1.4 (m,4H); δ1.7 (m,3H); δ3.1 (m,2H); δ3.4 (m,1H); 4.6 (broad,1H); δ8.0 (broad,1H); δ9.0 (s,1H); δ9.2 (s,2H). No purification was required. Yield was 90%.

EXAMPLE 4

Partitioning Studies: Enantiomer Distribution in a Two-Phase System

The feasibility of the liquid membrane model system was investigated by means of two-phase liquid-liquid partitioning experiments.

The chiral carrier molecule (L)-N-(1-naphthyl) leucine octadecyl ester was synthesized via the reaction of Example 1. The N-(3,5-dinitrobenzoyl)amino derivatives were prepared according to Examples 2 and 3. These racemate analytes were allowed to partition between a methanol:water solution and a dodecane solution containing the chiral carrier. Aliquots of the upper and lower layers were each analyzed by high performance liquid chromatography (HPLC), which chromatography analysis was performed with a Rainin HPX pump and a Milton-Roy UV monitor (254 nm). Integration of peak areas was obtained with an Altex model Chromatopac C-R1A data processing chart recorder (Shimadzu Corporation). The chiral stationary phase used was 33% (R)-enriched N-(2-naphthyl)alanine. Mobile phase for the analysis of the N-(3,5-dinitrobenzoyl)amino esters was 10% 2-propanol and 10% dichloromethane in hexane; for the analysis of N-(3,5-dinitrobenzoyl)leucine n-butyl amide, 20% 2-propanol and 10% methanol in hexane was used. Flow rate was 2.0 mL/minute.

Analysis of the enantiomeric purity of the carrier was performed on an (L)-N-(3,5-dinitrobenzoyl)leucine chiral stationary phase using 1% 2-propanol in hexane as mobile phase. Flow rate was 2.0 mL/minute. The integrated peak areas were used to compile the data presented in Table 1, below.

TABLE 1

Results of partitioning studies of N-(3,5-dinitrobenzoyl) amino acid derivatives between a 4:1 methanol:water solution and a solution of carrier in dodecane at 24° C.

| Analyte | Selectivity | | | Association Constant | | |
|---|---|---|---|---|---|---|
| | S/R[a] | EDC[b] | α[c] | K[S] | K[R] | K[S]/K[R] |
| leucine methyl ester | 9.5 | 16 | 13 | 2300 | 99 | 23 |
| leucine butyl ester | 4.7 | 20 | 16 | 2100 | 79 | 27 |
| leucine octyl ester | 1.9 | 20 | 16 | 1600 | 59 | 27 |
| leucine butyl amide | 12 | 26 | 31 | 2100 | 54 | 39 |
| alanine butyl ester | 7.7 | 13 | 9.2 | 1500 | 88 | 17 |
| valine butyl ester | 5.3 | 16 | 12 | 1100 | 41 | 27 |
| (α-methyl)valine butyl ester | 4.6 | 7 | 2.8 | 430 | 32 | 13 |

[a]The ratio of the S to the R-enantiomer in the dodecane/carrier solution at equilibrium
[b]EDC is the enantiomer distribution constant.
[c]The separation factor on a chiral stationary phase based on (L)-N-(1 naphtyl)leucine defined as $(t_2-t_0)/(t_1-t_0)$ where $t_2$ is the retention time of the more highly retained enantiomer, $t_1$ is the retention time of the least highly retained enantiomer, and $t_0$ is the void time of the HPLC column. Mobile phase: 10% 2-propanol in hexane; flow rate: 2.0 mL/minute.

In each case, a stock solution of the N-(3,5-dinitrobenzoyl) derivatized analytes listed in Table 1 was made up in 4:1 methanol:water. One mL of the stock solution was shaken in a screw cap test tube with one mL of a stock solution (20 mg/mL) of carrier in dodecane. The two phases were allowed to settle and stored until a time at which equilibration was determined to be complete. Since the analytes have U.V. active chromophores, the relative and absolute concentrations of enantiomers in the hydrocarbon and the aqueous phases were determined by HPLC as set forth in Example 4, with a U.V. detector. A 33% (S)-enriched N-(2-naphthyl)alanine chiral stationary phase was used for analytical determinations because low retention times resulted in more accurate integration. The integrated areas were used to calculate selectivities as well as association constants.

The ratio of the association constants, $K^S/K^R$, was an indication of the inherent selectivity of the carrier for the analytes while the ratio of enantiomers in the dodecane/carrier solution, S/R, was a reflection of the selectivity of the potential membrane.

The ratio $K^S/K^R$ decreased in the order: leucine=valine>alanine>(α-methyl)valine. This decrease was due to the nature of the chiral recognition mechanism. As the alkyl group on the stereogenic carbon of the analyte increased in size, the complex was destabilized due to steric interactions (compare $K^S$ values, Table 1). The R-complex was destabilized to a greater extent relative to the S-complex as the steric effect increased.

The S/R ratio in the dodecane phase was a proper indication of the selectivity of the membrane because it took into account the analyte which had diffused into the membrane by the achiral or unassisted process. For example, the S/R ratio for N-(3,5-dinitrobenzoyl)leucine butyl ester was greater S/R for the corresponding octyl ester while their $K^S/K^R$ ratios were equal. Two-phase partitioning experiments done in the absence of carrier showed that the octyl ester partitioned to a greater extent than the butyl ester in the dodecane phase. Thus, an additional amount of racemic octyl ester was present in the carrier/dodecane phase due to the achiral diffusion process and the ratio S/R was diminished with respect to the butyl ester.

Previous research into the selectivity of chiral liquid membranes has generated an expression which reflects the selectivity of a two-phase extraction. This expression is the "enantiomer distribution constant" (EDC), also referred to as the "separation factor" or "selectivity". It is the ratio of the distribution ratios of the two enantiomers in the two phases. EDC values are included here, Table 1, as a means of comparison to other results.

Also listed in Table 1 are the separation factors by HPLC on a chiral stationary phase based on (L)-N-(1-naphthy)leucine. The mobile phase composition was 10% 2-propanol in hexane at a flow rate of 2.0 mL/minute.

EXAMPLE 5

Liquid Membrane Separations

Medical-grade silastic tubing, 0.03 inches inner diameter by 0.65 inches outer diameter was obtained from Dow Corning. All solvents and reagents were obtained from Aldrich Chemical.

For each separation, an 8 foot length of silastic tubing was cut and immersed in dodecane (99%) for 2-3 hours, until the pores in the walls of the tubing had swollen. The outside of the tubing was toweled off to remove excess dodecane from the outer surface, and the inside allowed to drain. One end of the tubing was attached to a Beckman model 110A pump by means of a plastic connector. Forty-eight inches of tubing were wrapped around a spool which was then placed in the source vessel, or kettle. The remainder of the tubing was led to another spool. Forty-eight inches of tubing were wrapped around the second spool and placed in the receiving vessel, or kettle.

Dodecane was pumped from a reservoir through the tubing until it was filled. The reservoir was cleaned and filled with either 5 mL dodecane or 5 mL of a solution of chiral carrier ((L)-N-(1-naphthyl)leucine octadecyl ester, as prepared according to Example 1) in dodecane (20 mg/mL). Fifty milligrams of analyte (as prepared according to Example 2) were placed in the source kettle followed by 50 mL of a 4:1, methanol:water solution which had been saturated with dodecane. This constituted the source phase. The source phase was stirred and kept at a constant temperature by means of a water jacket. The dodecane or carrier solution was pumped through and recycled through the tubing at a rate of 1.0 mL/minute. Aliquots of 20 μL were taken from the interior of the tubing and analyzed by HPLC until an equilibrium with the source phase was achieved.

At this point, 50 mL of 4:1 methanol:water which had been saturated with dodecane was placed in the receiving vessel and stirred. Aliquots of 20μL were taken from the receiving vessel and analyzed by HPLC.

Using the above procedure with (±)-N-(3,5-dinitrobenzoyl)leucine butyl ester as the analyte, as prepared according to Example 2, the following results were obtained.

The incorporation of (±)-N-(3,5-dinitrobenzoyl) leucine butyl ester into the interior of the tubing was monitored over time by HPLC. The increase in the concentration of both enantiomers in the liquid membrane over time in indicated in FIG. 6. The slowest rate is observed when no carrier is present in the liquid membrane (curve a). The rate of incorporation of both enantiomers (curves b,c) is increased when the carrier is present and the ratio of these rates is 9:1 (S:R).

The liquid membrane was recirculated through the interior of the tubing until an equilibrium was achieved between the liquid membrane and the source phase. At this point, 50 mL of 4:1 methanol:water which had been saturated with dodecane was added to the receiving kettle. The decrease in the concentrations of the isomers in kettle 1 was monitored over time, FIG. 7, as well as the increase in concentrations of the isomers in kettle 2, FIG. 8.

The rate at which the more strongly complexed S-enantiomer was incorporated into the receiving phase, FIG. 8, decreased as the supply of S-enantiomer in the liquid membrane was depleted. Thus, the rate of transport of the R-enantiomer could "catch up" to and actually overtake the rate of transport of the S-enantiomer. This resulted in a diminished enantiomeric excess in the second kettle over time, FIG. 9.

For any given separation there is a time at which the optimum transport amount is achieved at the lowest cost to enantiomeric enrichment. This must be determined for every analyte. In the case of the experiment described here, an arbitrary stopping point was repeated in the same manner but stopped at the designated time, 1700 minutes. Collecting the source and receiving phases and evaporating them to dryness resulted in a mixture of N-(3,5-dinitrobenzoyl)leucine butyl ester and some carrier which had leached out of tubing. The enriched analyte was separated from the carrier impurity by flash silica gel chromatography. The amount of pure material recovered from the source phase was 30.9 mg with an enantiomeric excess of 52.4% (R); 17.4 mg was recovered from the receiving phase in an enantiomeric excess of 57.3% (S).

EXAMPLE 6

Rates of Transport

A series of N-(3,5-dinitrobenzoyl)amino acid derivatives, as prepared according to Example 2, was used to study the efficacy of the separation process by the liquid membrane described. A means of comparing both the rates of transport and the selectivity of the transport process was desired. Aliquots from the kettles and reservoir were periodically withdrawn and analyzed by HPLC. Since the analytes have U.V. active chromaphores, the relative and absolute concentrations of enantiomers in the hydrocarbon and the aqueous phases were determined (by HPLC, as set forth in Example 4) with a U.V. detector. A 33% (S)-enriched N-(2-naphthyl)alanine chiral stationary phase was used for analytical determinations because low retention time resulted in more accurate integration. The integrated areas were used to calculate selectivities as well as association constants. It was observed that the rate of transport from the liquid membrane to the receiving phase was time dependent, FIG. 8. It was also observed that for a certain period of time, the change in the concentration of analyte in the receiving phase is linear with respect to time, FIG. 10. Thus the "initial" rate of transport is determined from the slope of the curve for the graph of concentration vs. time in the receiving phase. The ratio of the rate of transport of the faster moving enantiomer to the slower is a relative measure of the selectivity.

The rate of transport, FIG. 10, for the S-enantiomer of N-(3,5-dinitrobenzoyl)leucine butyl ester is $5.1 \times 10^{-7}$ M/minute and for the R-enantiomer is $1.3 \times 10^{-7}$ M/minute; the ratio of these rates is 3:9.

A series of experiments directed to the transport of other N-(3,5-dinitrobenzoyl)amino esters was performed with a variety of analytes, the experiments conducted using the procedure described above, as illustrated with N-(3,5-dinitrobenzoyl)leucine butyl ester. A list of the initial rates of transport into the receiving phase as well as the ratio of these rates is given in Table 2, below. The relative selectives are analoguous to the S/R ratios in the dodecane/carrier solutions determined in the two-phase partition studies, Table 1. The enantiomeric excesses (e.e.'s) corresponding to these ratios of rates are listed also.

TABLE 2

The rates of transport from the liquid membrane to the receiving phase of various N-(3,5-dinitrobenzoyl)amino acid derivatives. Rates are in units of (mol × L$^{-1}$ × min$^{-1}$) × 10$^7$. The ratio of rates as well as the corresponding enantiomeric excesses in the receiving phase.

| Analyte | Rate, S-enantiomer | Rate, R-enantiomer | Ratio of Rates | e.e. |
|---|---|---|---|---|
| alanine butyl ester | 1.8 | .37 | 4.9 | 66% |
| valine butyl ester | 3.3 | .99 | 3.3 | 53% |
| (α-methyl)valine butyl ester | 2.2 | .84 | 2.6 | 44% |
| leucine methyl ester | 3.8 | .53 | 7.2 | 76.% |
| leucine butyl ester | 5.1 | 1.3 | 3.9 | 59% |
| leucine octyl ester | 8.4 | 4.9 | 1.7 | 26% |
| leucine butyl amide | 1.1 | .14 | 7.6 | 77% |
| leucine butyl ester (33% S-enriched) | 4.9 | .71 | 6.9 | 75% |

As was seen in the two-phase partition studies of Example 4, the selectivity decreases as the lipophilicity of the analyte increases. It was determined in experiments identical to that used to generate FIG. 6 (curve a) as described in Example 5 for N-(3,5-dinitrobenzoyl)-leucine butyl ester, in which the carrier was excluded that the rate of transport into the membrane by the achiral mechanism increases with increasing lipophilicity of the analyte. The rate of achiral transport into the membrane of N-(3,5-dinitrobenzoyl)leucine methyl ester was $0.72 \times 10^{-7}$ mol×L$^{-1}$×min$^{-1}$; butyl ester, $2.7 \times 10^{-7}$ mol×L$^{-1}$×min$^{-1}$; octyl ester, $12 \times 10^{-7}$ mol×L$^{-1}$×min$^{-1}$. Thus the percentage of racemic material collected in the membrane increased as the lipophilicity of the analyte increased and the result was a decrease in selectivity.

If the source phase was enriched with S-enantiomer at the start of the experiment, the end result was an increase in the ratio of transport rates into the receiving phase. Compare, Table 2, a racemic N-(3,5-dinitrobenzoyl) leucine butyl ester source phase (ratio of rates 3.9) to a 33% (S)-enriched source phase (ratio of rates 6.9).

EXAMPLE 7

Carrier Concentration Effects

The effect of the carrier concentration of the rate of transport and the selectivity was studied. A series of experiments was performed using the N-(3,5-dinitrobenzoyl) leucine butyl ester and increasing the concentration of the carrier by 5× and 25×. The rates of transport as well as corresponding enantiomeric increases (e.e.'s) in the membrane and receiving phase are given in Tables 3 and 4. The amount of analyte used in each case was 50 mg in 50 mL 4:1 methanol:water. The temperature of both kettles was maintained at 18° C. The experiments were performed identically to those used to generate curves b and c of FIG. 6, as previously described in Example 5.

TABLE 3

The effect of carrier concentration on the rates of incorporation of N-(3,5-dinitrobenzoyl)leucine butyl ester into the liquid membrane from the source phase.

| Carrier Concentration | Rate of Transport (mol × L$^{-1}$ × min$^{-1}$ × 10$^7$) S | R | Ratio of Rates | e.e. |
|---|---|---|---|---|
| 4 mg/mL | 6.3 | .77 | 8.2 | 78% |
| 20 mg/mL | 36 | 3.9 | 9.2 | 80% |
| 100 mg/mL | 144 | 12 | 12 | 85% |

TABLE 4

The effect of carrier concentration on the rates of incorporation of N-(3,5-denitrobenzoyl))leucine butyl ester into the receiving phase from the membrane after an equilibrium has been achieved between the source phase and the membrane.

| Carrier Concentration | Rate of Transport (mol × L$^{-1}$ × min$^{-1}$ × 10$^7$) S | R | Ratio of Rates | e.e. |
|---|---|---|---|---|
| 4 mg/mL | 2.2 | .74 | 3.0 | 50% |
| 20 mg/mL | 5.5 | 1.4 | 3.9 | 59% |
| 100 mg/mL | 5.7 | 1.8 | 3.2 | 52% |

The results presented in Table 3 show that the ratio of the enantiomers in the carrier solution at equilibrium with the source phase increased with the concentration of carrier. This was due to the fact that a greater degree of complexation was allowed when there was a higher concentration of carrier. Thus the relative amount of analyte present in the carrier solution uncomplexed (and therefore, racemic) was minimized.

The results presented in Table 4 show that the ratio of the S- to R-enantiomers in the receiving phase increased with the increase in carrier concentration except at the highest concentration examined where there was a decrease in S/R. Since the R-complex was more easily dissociated than the receiving phase than in the membrane. Thus, at high concentration of carrier, the dissociation of the S-complex was further hindered while the dissociation of the R-complex was hot. The overall effect was an increase in transport of the R-enantiomer relative to the S-enantiomer and a decrease in S/R in the receiving phase.

EXAMPLE 8

Temperature Effects

The effect of temperature on the transport process was also studied. The experiments performed were identical to those previously described using a carrier concentration of 20 mg/mL and N-(3,5-dinitrobenzoyl)-leucine butyl ester as the analyte. The results for an experiment in which both source and receiving kettles were maintained at 18° C. are listed on Table 5. Those for an experiment in which the first (source) kettle is at 0° C. and the second (receiving) kettle is at 50° C. are listed in Table 6.

TABLE 5

The rates of transport of N-(3,5-dinitrobenzoyl) leucine butyl ester from the source phase to the liquid membrane and, after an equilibrium was achieved, from the membrane to the receiving phase.

| | Temp. | Rate of Transport (mol × L$^1$ × min$^{-1}$ × 10$^7$) S | R | Ratio of Rates |
|---|---|---|---|---|
| Source phase to membrane | 18° C. | 36 | 3.9 | 9.2 |
| Membrane to receiving phase | 18° C. | 5.5 | 1.4 | 3.9 |

TABLE 6

The rates of transport of N-(3,5-dinitrobenzoyl) leucine butyl ester from the source phase to the liquid membrane and, after an equilibrium was achieved, from the membrane to the receiving phase.

| | Temp. | Rate of Transport (mol × L$^1$ × min$^{-1}$ × 10$^7$) S | R | Ratio of Rates |
|---|---|---|---|---|
| Source phase to membrane | 0° C. | 52 | 3.7 | 14 |
| Membrane to receiving phase | 50° C. | 17 | 1.8 | 9.6 |

Comparing the results in Tables 5 and 6 show that lowering the temperature of the first kettle had the effect of stabilizing the enantiomer-carrier complex. It also had the effect of diminishing the rate of achiral diffusion into the membrane as has been determined by separate experiments in which the carrier was excluded. Together, these effects resulted in an enhancement of the selectivity of the transport process. The enantiomeric excess in the membrane after equilibration at 18° C. was 80% while at 0° C. it was increased to 87%.

The increase in the temperature of the receiving phase served to improve the efficiency of the dissociation process. This resulted in an enhanced rate of transport from the membrane to the receiving phase. The net effect of the temperature differential was an increase in the overall selectivity from 3.9 (59% e.e.).

A final experiment was performed in which both the temperature differential and the effect of an enantiomerically enriched source phase were combined. The results listed in Table 7 are for an experiment in which the source phase was enriched 11.5% in the S-enantiomer of N-(3,5-dinitrobenzoyl))leucine butyl ester. The first (source) kettle was maintained at 0° C. while the second (receiving) kettle was heated to 60° C. The final ratio (14.2) corresponds to an enantiomeric excess of 87%.

TABLE 7

The rates of transport of N-(3,5-dinitrobenzoyl) leucine butyl ester from the source phase (enriched 11.5% S) to the liquid membrane and, after an equilibrium was achieved, from the membrane to the receiving phase.

| | Temp. | Rate of Transport (mol × L$^1$ × min$^{-1}$ × 10$^7$) S | R | Ratio of Rates |
|---|---|---|---|---|
| Source phase to membrane | 0° C. | 55 | 3.2 | 17.2 |
| Membrane to receiving phase | 60° C. | 27 | 1.9 | 14.2 |

What is claimed is:

1. A process for the separation of enantiomers comprising:
   (a) providing an alternative to processes that separate enantiomers by way of enzyme-based techniques that involve stereoselective reaction wherein said alternative separates a liquid membrane containing a chiral carrier from a mixture of enantiomers having first and second optical configurations with a first semi-permeable barrier at a first location, said barrier being substantially impregnated with said liquid membrane containing said chiral carrier, under conditions effective to form in said barrier a stable complex between said chiral carrier and an enantiomer having said first optical configuration and cause said stable complex to pass into said liquid membrane;

(b) passing said liquid membrane containing the stable complex from said first location to a second location;

(c) contacting said liquid membrane containing the stable complex with a first surface of a second semi-permeable barrier at said second location under conditions effective to cause said liquid membrane containing the stable complex to impregnate said second barrier, dissociate said stable complex in said barrier and the enantiomer having said first optical configuration to pass a second surface of said barrier at said second location.

2. The process of claim 1 further comprising dissolving said mixture of enantiomers at said first location in a first liquid, and dissolving said enantiomer having said first optical configuration in a second liquid in contact with said second surface of said second barrier at said second location.

3. The process of claim 2 wherein said first liquid and second liquid are polar.

4. The process of claim 3 wherein said first and second liquids are a mixture of alcohol and water.

5. The process of claim 4 wherein the mixture of alcohol and water is in a ratio of about 10:1 alcohol to water to about 0.0:1 alcohol to water.

6. The process of claim 5 wherein the mixture is comprised of methanol and water at a ratio of about 4:1.

7. The process of claim 1 wherein said first and second barriers are comprised of a microporous or gel-type materials, or combinations thereof.

8. The process of claim 7 wherein said microporous material is silicone rubber, polyacrylonitrile, polypropylene, polyethylene, polysulfone or combinations thereof.

9. The process of claim 7 wherein said gel-type material is a regenerated cellulose polypropylene, polyethylene, silicone rubber of combinations thereof.

10. The process of claim 1 wherein said conditions at said first location include a temperature facilitating formation of the stable complex.

11. The process of claim 1 wherein said conditions at said second location include a temperature facilitating dissociation of the stable complex.

12. The process of claim 1 wherein said first and second barriers are comprised of at least one tube.

13. The process of claim 1 wherein said first and second barriers are in a hollow fiber geometry.

14. The process of claim 1 wherein said second barrier is contiguous with said first barrier.

15. The process of claim 1 wherein the liquid membrane is non-polar.

16. The process of claim 15 wherein the liquid membrane is a $C_6$ to $C_{16}$ alkane.

17. The process of claim 16 wherein the alkane is $C_{12}$.

18. The process of claim 1 wherein the chiral carrier is a derivatized amino acid.

19. The process of claim 18 wherein the derivatized amino acid is (S)-N-(1-naphthyl)leucine octadecyl ester.

20. The process of claim 1 wherein said enantiomers are amino acids, amino esters, sulfoxides, alcohols, amines sulfonic acids, or derivatives thereof.

21. The process of claim 20 wherein said enantiomer is an N-(3,5-dinitrobenzoyl)α-amino acid or ester.

22. The process of claim 1 wherein said enantiomer having said first optical configuration is (S)-N-(3,5-dinitrobenzoyl)leucine n-butyl ester.

23. A process for separating enantiomers having first and second optical configurations comprising:

(a) providing an alternative to processes that separate enantiomers by way of enzyme-based techniques that involve stereoselective reactions wherein said alternative comprises placing into a source vessel enantiomers having first and second optical configurations and a first liquid in which said enantiomers are soluble, said first liquid and enantiomers being at a first temperature;

(b) placing into a receiving vessel a second liquid, said second liquid being at a second temperature;

(c) providing at least one semi-permeable tube, said at least one tube being disposed within said source vessel and extending to and being disposed within said receiving vessel;

(d) passing through said at least one tube, in a direction of said source vessel to said receiving vessel, a liquid membrane and a chiral carrier under conditions effective to form a stable complex between said chiral carrier and an enantiomer having said first optical configuration within a first pore of said at least one tube, said first pore being located in a portion of said at least one tube disposed within said source vessel, said stable complex formation being facilitated by said first temperature;

(e) passing said stable complex from said first pore into the liquid membrane so as to transport said stable complex through said at least one tube from said source vessel to said receiving vessel under conditions effective to dissociate said stable complex into said chiral carrier and the enantiomer having said first optical configuration, within a second pore of said at least one tube said second pore being located in a portion of said at least one tube disposed within said receiving vessel, and said dissociation being facilitated by said second temperature; and (f) releasing said enantiomer having said first optical configuration into said receiving vessel.

24. The process of claim 23, further comprising recovering said enantiomer having said first optical configuration from said receiving vessel.

25. The process of claim 23, further comprising recovering an enantiomer having said second configuration from said source vessel.

26. The process of claim 23, wherein the first temperature is in the range of about $-10°$ C. to about $10°$ C.

27. The process of claim 23, wherein the second temperature is in the range of about $40°$ C. to about $60°$ C.

28. The process of claim 23, further comprising circulating said liquid membrane and said chiral carrier from said receiving vessel back to the portion of said at least one tube disposed within said source vessel.

29. An apparatus for the separation of enantiomers comprising:

(a) means for providing an alternative to separating enantiomers by way of enzyme-based techniques that involve stereoselective reactions, said means including, at least one first semi-permeable barrier which can substantially separate a mixture of enantiomers having first and second optical configurations from a liquid membrane containing a chiral carrier at a first location, said first barrier capable of being impregnated with said liquid membrane containing said chiral carrier to form a stable complex between said chiral carrier and an enantiomer having said first optical configuration in said barrier and to pass said stable complex into said liquid membrane;

(b) means for passing said liquid membrane containing said stable complex from said first location to a second location;

(c) at least one second semi-permeable barrier at said second location, said second barrier capable of being impregnated from a first surface with said liquid membrane containing said stable complex to dissociate said stable complex in said second barrier and pass said enantiomer having said first optical configuration to a second surface of said second barrier.

30. The apparatus of claim 29 further comprising temperature control means for said first and second locations.

31. The apparatus of claim 30, wherein said temperature control means operate to facilitate the formation of said complex.

32. The apparatus of claim 30, wherein said temperature control means operate to facilitate the dissociation of said complex.

33. The apparatus of claim 29 further comprising means for recirculating said liquid membrane and said dissociated chiral carrier from said second location to said first location.

34. The apparatus of claim 29 wherein said at least one first barrier and said at least one second barrier comprise a microporous or gel-type material, or combinations thereof.

35. The apparatus of claim 34 wherein said microporous material is silicone rubber, polyacrylonitrite, polypropylene, polyethylene, or combinations thereof.

36. The apparatus of claim 34 wherein said gel-type material is ia regenerated cellulose.

37. The apparatus of claim 34 wherein said at least one first barrier and said at least one second barrier are in a hollow fiber geometry.

38. The apparatus of claim 34 wherein said at least one second barrier is contiguous with said at least one first barrier.

39. An apparatus for separating enantiomers having first and second optical configurations which comprises:

(a) means for providing an alternative to separating enantiomers by way of enzyme-based techniques that involve stereoselective reactions, said means including at least one semi-permeable conduit having at least one first pore at a first location and at least one second pore at a second location;

(b) means for contacting said enantiomers having said first and second optical configurations with the outside surface of said conduit at said first pore to form a stable complex between an enantiomer having said first optical configuration and a chiral carrier, said stable complex formation occurring within said first pore;

(c) means for passing a liquid membrane through said conduit from said first location to said second location such that said stable complex is transported to said second location after moving into said fluid flow from said first pore;

(d) means for receiving at said second location, said enantiomer having said first optical configuration after dissociation of said stable complex into said enantiomer having said first optical configuration and said chiral carrier, said dissociation occurring within said second pore.

* * * * *

UNITED STATES PATENT AND TRADEMARK OFFICE
CERTIFICATE OF CORRECTION

PATENT NO. : 5,080,795

DATED : January 14, 1992

INVENTOR(S) : William H. Pirkle, et al.

It is certified that error appears in the above-identified patent and that said Letters Patent is hereby corrected as shown below:

On the Title Page item [56], after "435/183" insert --4,754,089   6/28/88   Matson, et al.

Armstrong, D.W., and Jin, H. I., "Enrichment of Enantiomers and Other Isomers with Aqueous Liquid Membranes Containing Cyclodextrin Carriers, Anal. Chem. 1987, Volume 59: Pages 2237-2241.

Yamaguchi, T., Nishimura, K., Shinbo, T. and Sugiura, M., "Enantiomer Resolution of Amino Acids by a Polymer-Supported Liquid Membrane Containing a Chiral Crown Ether", Chemistry-Letters, 1985, Pages 1549-1552.

Kruger, G., Grotzinger and Berndt, H., "Enantiomeric Resolution of Amino Acid Derivatives on Chiral Stationary Phases by High-Performance Liquid Chromatrography", . of Chromatography, 1987, Volume 397: Pages 223-232.

Lehn, J. M. Moradnour, A. and Behr, J. P., "Antiport Regulation of Carrier Mediated Chiroselective Transport Through a Liquid Membrane", J. of Amer. Chem. Soc., April 30, 1975, Volume 97: Page 9.

Berndt, H. and Kruger, G., "Resolution of Enantiomeric Amino Acid Derivatives by High-Performance Liquid CHromatography on Chiral Stationary Phases", J. of Chromatography, 1985, Volume 348: Pages 275-279.

UNITED STATES PATENT AND TRADEMARK OFFICE
CERTIFICATE OF CORRECTION

PATENT NO. : 5,080,795

DATED : January 14, 1992

INVENTOR(S) : William H. Pirkle, et al.

It is certified that error appears in the above-identified patent and that said Letters Patent is hereby corrected as shown below:

Bayer, E., Spivakov, B. Ya and Geckeler, K., "Poly(Ethyleneimine) as Complexing Agent for Separation of Metal Ions Using Membrane Filtration", Polymer Bulletin, 1985, Volume 13: Pages 307-311.

Geckler, K. E., Bayer, E., Spivakov, B. Ya, Shkinev, V.M. and Vorob'eva, G. A., "Liquid Phase Polymer-Based Rentention, A New Method for Separation and Preconcentration of Elements", Analytica Chimica Acta, 1986, Volume 189: Pages 285-292.

Yamaguchi, T., Nishimura, K., Shinbo, T. and Sugiura, M., "Amino Acid Transport Through Supported Liquid Membranes:Mechanism and its Application to Enantiomeric Resolution", Biochemistry and Bioenergetics, 1988, Volume 20: Pages 109-123.--

Column 10, line 51, "tubin-g" should read as --tubing--

Column 12, line 7: "Na" should read as --$Na_2SO_3$,--

UNITED STATES PATENT AND TRADEMARK OFFICE
CERTIFICATE OF CORRECTION

PATENT NO. : 5,080,795

DATED : January 14, 1992

INVENTOR(S) : William H. Pirkle, et al.

It is certified that error appears in the above-identified patent and that said Letters Patent is hereby corrected as shown below:

Column 13, line 19: "1H" should read as --$^1$H--

Column 13, line 25: "1H" should read as --$^1$H--

Column 13, line 49: "C; MHz," should read as --C; $^1$H NMR (200 MHz,--

Column 18, line 42: "of" should read as --on--

Column 18, lines 47-48: "increases" should read as --excesses--

Column 19, line 34: "hot" should read as --not--

Column 20, line 29: "e.e.)." should read as --2.2.) to 9.6 (81% e.e.).--

Column 24, line 2, Claim 36: "ia" should read as --a--

Signed and Sealed this

Twenty-sixth Day of October, 1993

Attest:

BRUCE LEHMAN

*Attesting Officer*    *Commissioner of Patents and Trademarks*